| (12) | United States Patent | (10) Patent No.: | US 10,384,049 B2 |
|---|---|---|---|
| | Stanton et al. | (45) Date of Patent: | Aug. 20, 2019 |

(54) TUBING CLAMP

(71) Applicant: Halkey-Roberts Corporation, St. Petersburg, FL (US)

(72) Inventors: Katherine J. Stanton, St. Petersburg, FL (US); Stephen P. Bello, Clearwater, FL (US)

(73) Assignee: Halkey-Roberts Corporation, St. Petersburg, FL (US)

( * ) Notice: Subject to any disclaimer, the term of this patent is extended or adjusted under 35 U.S.C. 154(b) by 35 days.

(21) Appl. No.: 15/204,309

(22) Filed: Jul. 7, 2016

(65) Prior Publication Data

US 2017/0009895 A1 Jan. 12, 2017

Related U.S. Application Data

(60) Provisional application No. 62/189,559, filed on Jul. 7, 2015.

(51) Int. Cl.
*F16K 7/06* (2006.01)
*A61M 39/28* (2006.01)

(52) U.S. Cl.
CPC ............ *A61M 39/28* (2013.01); *F16K 7/063* (2013.01)

(58) Field of Classification Search
CPC . F16K 7/066; F16K 7/06; F16K 7/063; F16K 7/065; F16K 7/061; A61M 39/28; A61M 39/286; A61M 39/284; A61M 39/285; A61B 17/122; Y10T 24/44; Y10T 24/44983
USPC .................................... 251/4, 9, 10; 604/250
See application file for complete search history.

(56) References Cited

U.S. PATENT DOCUMENTS

| 4,429,852 | A | 2/1984 | Tersteegen et al. |
|---|---|---|---|
| 4,453,295 | A | 6/1984 | Laszczower |
| 5,203,056 | A | 4/1993 | Funk et al. |
| 5,238,218 | A * | 8/1993 | Mackal ................. A61M 39/28 251/10 |
| 6,234,448 | B1 * | 5/2001 | Porat ................... A61M 39/284 251/10 |
| 8,262,639 | B2 * | 9/2012 | Mathias .............. A61M 39/284 604/250 |
| 8,801,677 | B2 * | 8/2014 | Wallin ................ A61M 39/284 251/10 |
| 9,079,008 | B2 | 7/2015 | Nipro et al. |
| 2008/0051731 | A1 | 2/2008 | Schweikert |
| 2009/0171380 | A1 * | 7/2009 | Whiting ............... A61B 17/122 606/158 |
| 2010/0152681 | A1 | 6/2010 | Mathias |
| 2011/0130629 | A1 | 6/2011 | Watanabe |

(Continued)

FOREIGN PATENT DOCUMENTS

| EP | 2332611 A1 | 8/2011 | |
|---|---|---|---|
| WO | WO 2013177537 A1 * | 11/2013 | .............. F16K 7/06 |

*Primary Examiner* — Craig J Price
*Assistant Examiner* — Andrew J Rost
(74) *Attorney, Agent, or Firm* — GrayRobinson, P.A.

(57) ABSTRACT

A clamp for flexible tubing such as medical tubing or micro-tubing. The clamp comprises a clam-shell design having lateral non-opposing sidewalls that prevent the micro-tubing from bending out from under the mating clamping anvils when closed. The lateral non-opposing sidewalls of the clamp are non-opposing in order to facilitate injection molded in two halves of an injection mold without the use of additional slides.

16 Claims, 10 Drawing Sheets

(56) References Cited

U.S. PATENT DOCUMENTS

| | | | | |
|---|---|---|---|---|
| 2012/0232497 A1* | 9/2012 | Singh | .................. | A61M 39/284 |
| | | | | 604/250 |
| 2013/0310768 A1* | 11/2013 | Ebara | .................... | A61M 5/168 |
| | | | | 604/250 |
| 2014/0074047 A1* | 3/2014 | Calderon | .............. | A61M 39/28 |
| | | | | 604/250 |

\* cited by examiner

TUBING CLAMP

CROSS REFERENCE TO RELATED APPLICATIONS

This invention claims the benefit of provisional application Ser. No. 62/189,559, filed Jul. 7, 2015, the disclosure of which is hereby incorporated by reference herein.

BACKGROUND OF THE INVENTION

Field of the Invention

This invention relates to a clamp for hoses or flexible tubing. More particularly, this invention relates to tubing clamps commonly used in the medical industry.

Description of the Background Art

Presently, there exist many types of clamps for clamping onto a tubing or other flexible member to at least partially obstruct fluid flow through the tubing or to completely close-off fluid flow through the tubing. One particular industry that requires the use of tubing clamps is the medical industry wherein clamps are used widely as tubing clamps in intravenous administration sets, catheterization kits, and many other medical assemblies.

One of the most common types of tubing clamp in the medical industry comprises a clam-shell design having upper and lower arms joined together by a living hinge. The medical tubing is positioned between the upper and lower arms which are allowed to clamp onto the tubing by means of the living hinge. Typically, the upper arm includes a pointed end that engages into teeth formed in the end of the lower arm to achieve a complementary ratchet mechanism such that the anvils of upper and lower body portions may be clamped onto the medical tubing to reduce fluid flow or to entirely close off all fluid flow. Further, the most widely used tubing clamp comprises a longitudinal hole formed through the living hinge and the ratcheting portions of the lower arm such that the tubing is threaded therethrough in alignment with mating clamping anvils to squeeze closed the tubing therebetween.

Importantly, surgical micro-tubing had led to the development of lateral opposing sidewalls that confine the micro tubing to rest between the unclamped anvils thereby precluding the micro tubing from otherwise creeping out between the anvils before they are clamped together.

Figure 1:
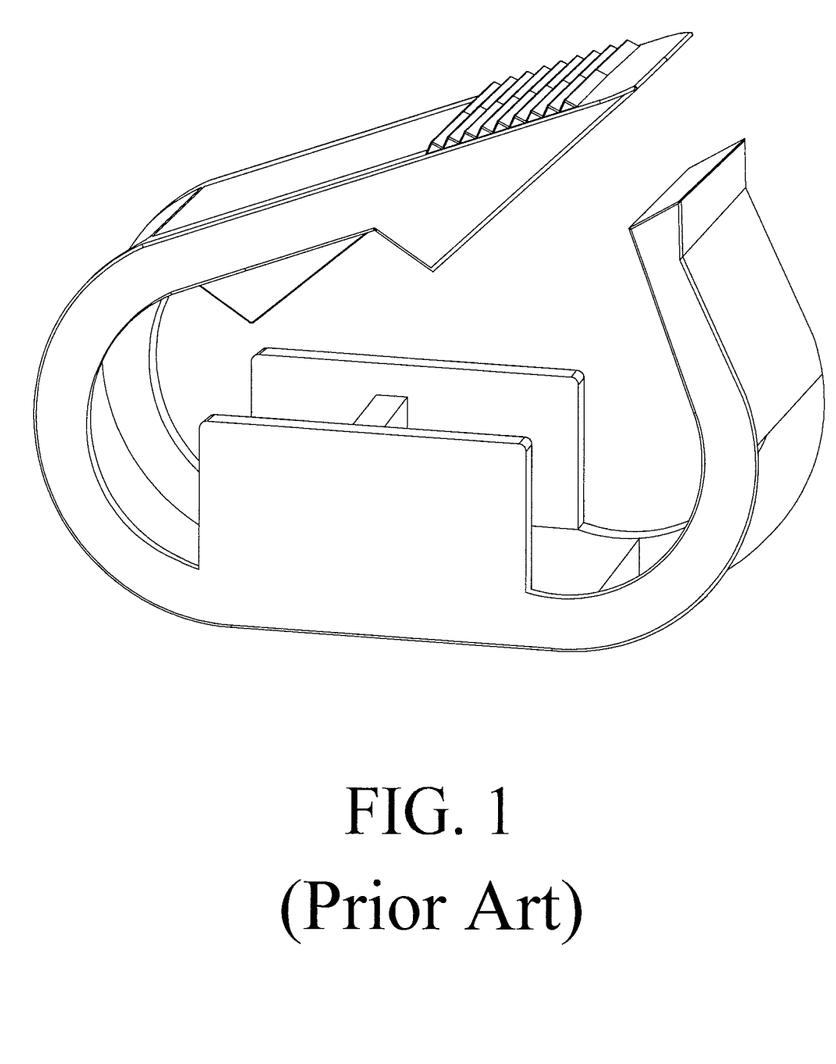
FIG. 1 is a perspective view of a prior art tubing clamp having lateral sidewalls that are directly opposing one another.
Figure 2A:
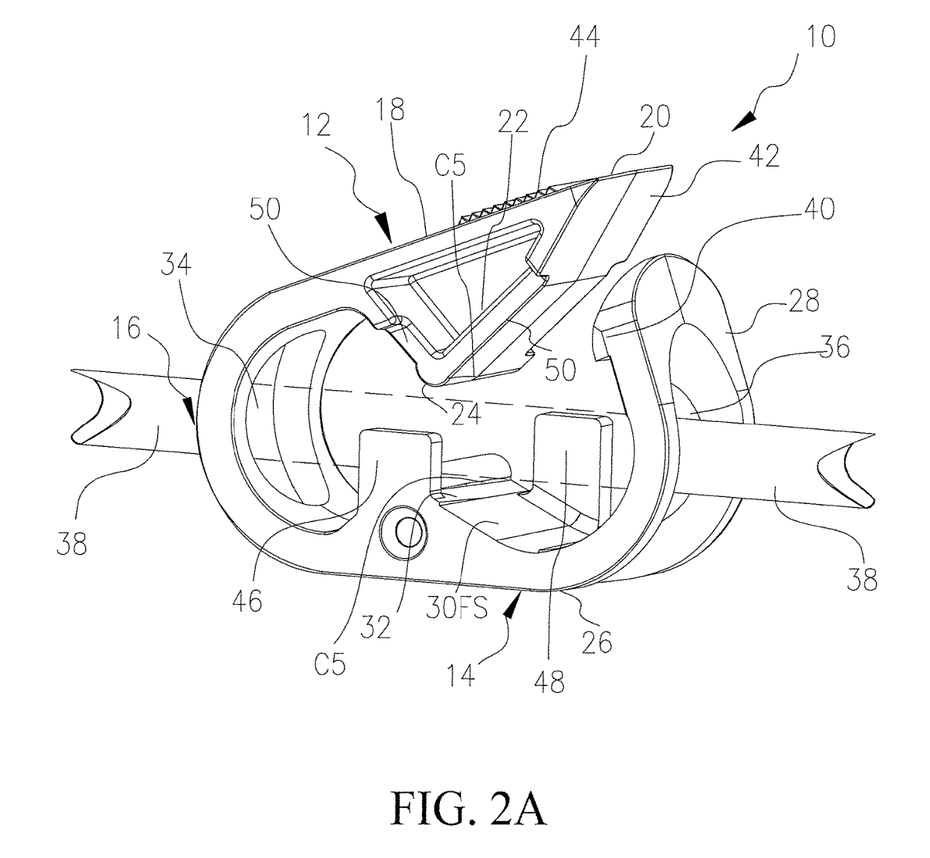
FIG. 2A is a right perspective view of a first embodiment of the tubing clamp of the invention having two lateral sidewalls that are not directly opposing one another.
Figure 2B:
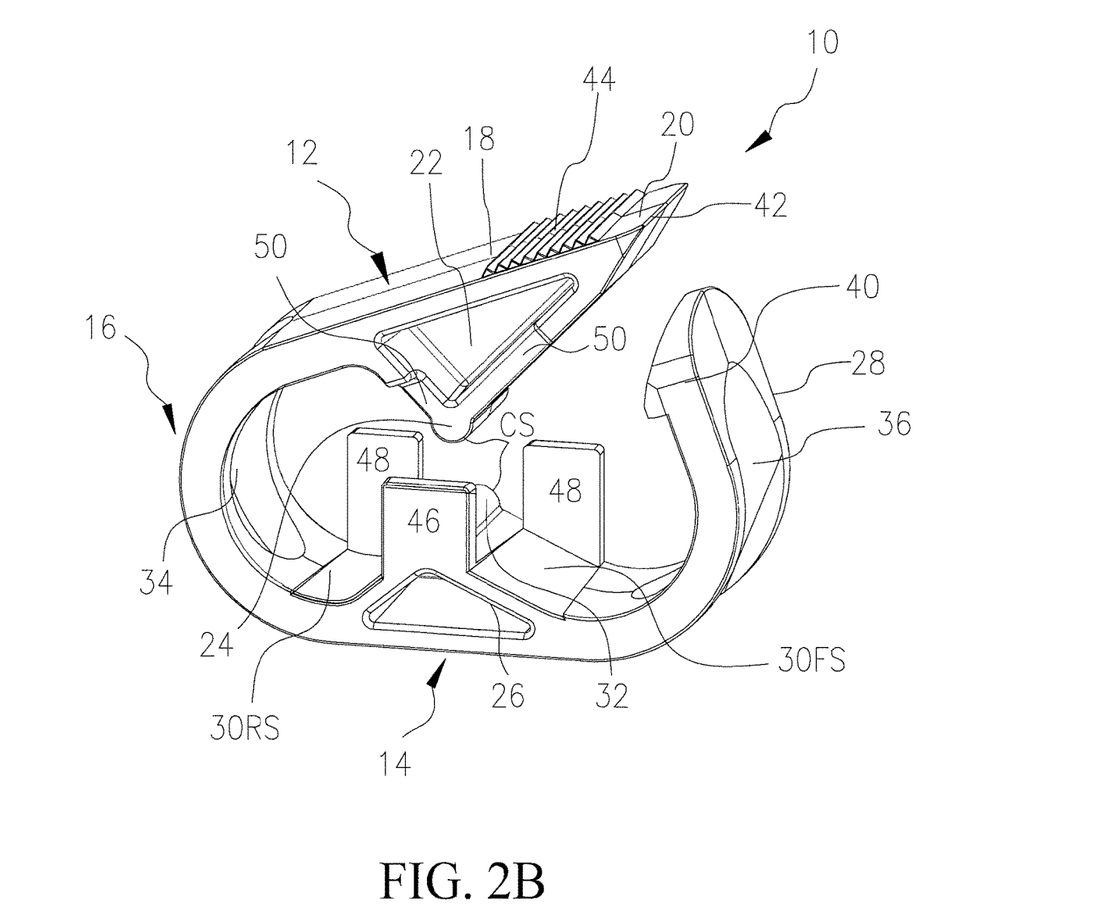
FIG. 2B is a right perspective view of a second embodiment the tubing clamp of the invention having three lateral sidewalls that are not directly opposing one another.
Figure 3A:
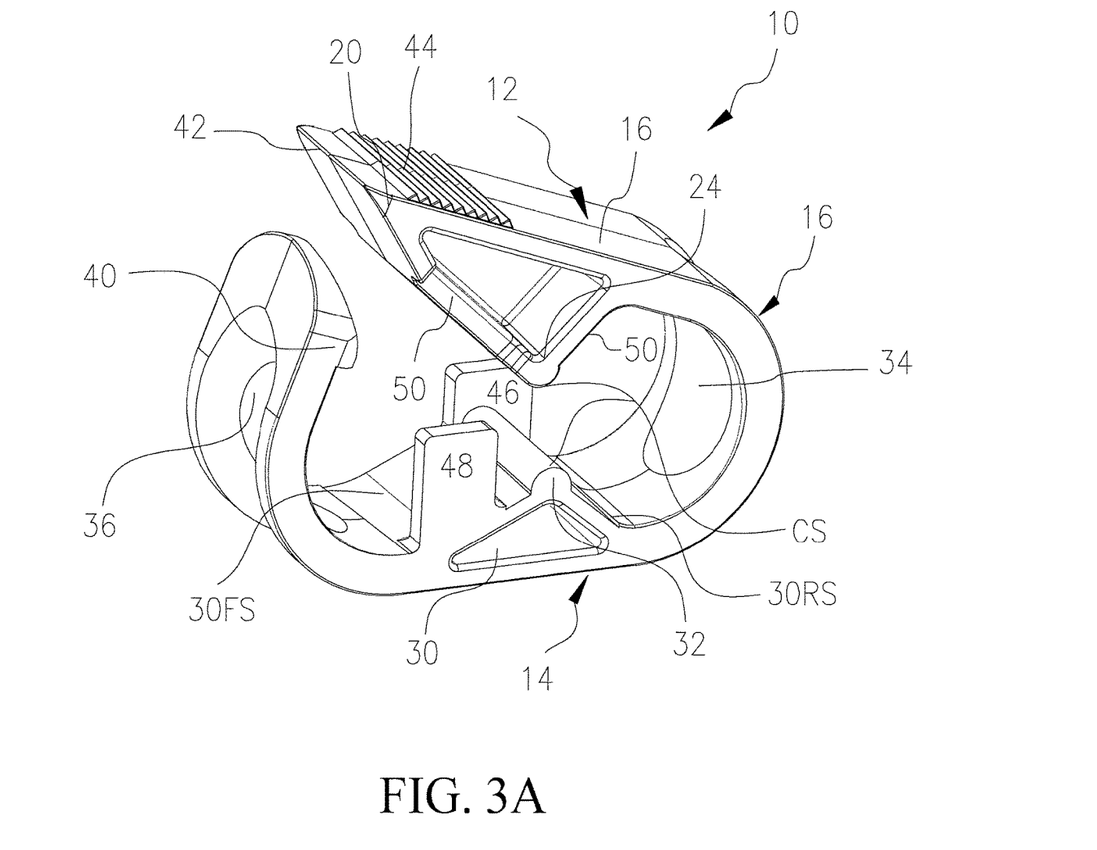
FIG. 3A is a left perspective view of a first embodiment of the tubing clamp of the invention having two lateral sidewalls that are not directly opposing one another.
Figure 3B:
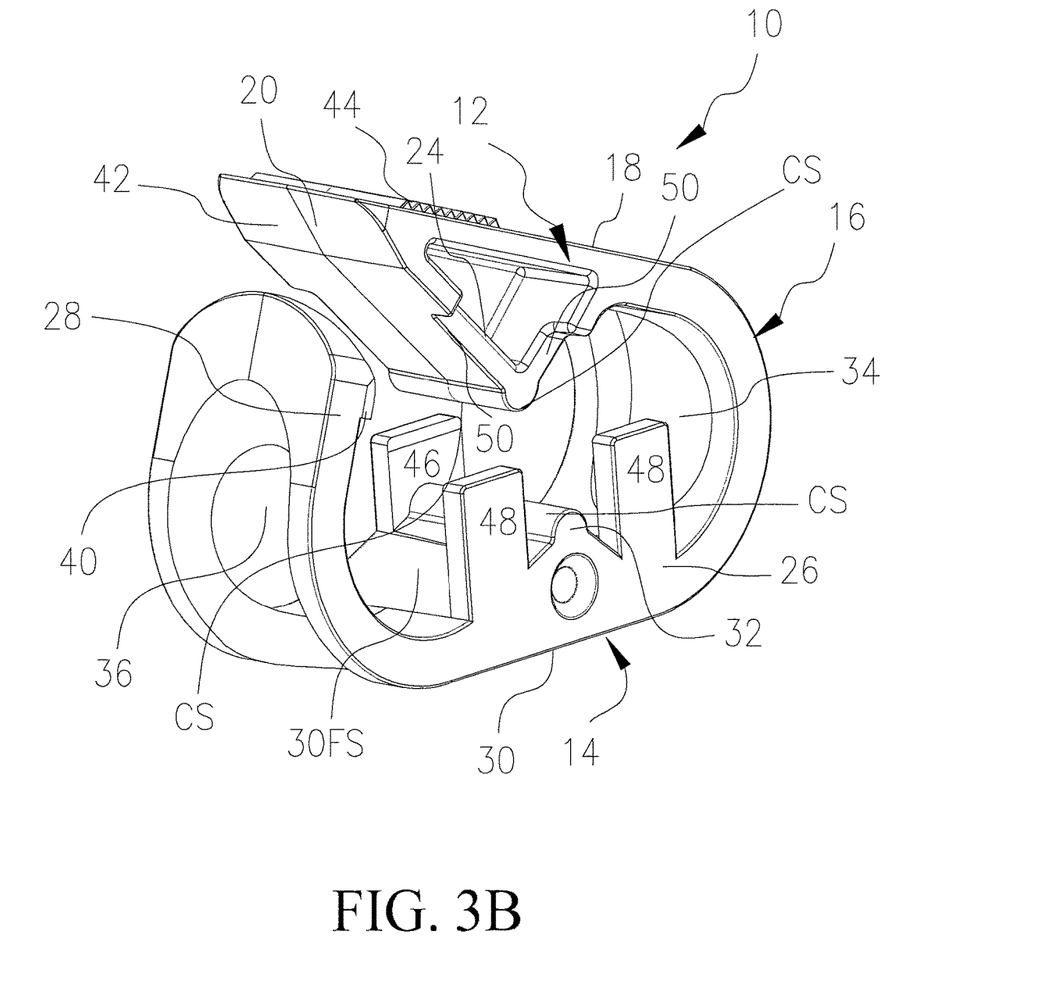
FIG. 3B is a left perspective view of a second embodiment the tubing clamp of the invention having three lateral sidewalls that are not directly opposing one another.

The entirety of the tubing clamp is typically manufactured as a one-piece injection-molded assembly. Accordingly, conventional molding techniques are preferably employed with minimal slides. As shown in FIG. 1, known tubing clamps with opposing sidewalls require too many slides and other complex molding techniques.

Therefore, an object of this invention to provide an improvement which overcomes the aforementioned inadequacies of the prior art devices and provides an improvement which is a significant contribution to the advancement of the tubing clamp art.

Another object of this invention is to provide a tubing clamp having non-opposing sidewalls that may be injection molded without slides.

Another object of this invention is to provide a tubing clamp having non-opposing sidewalls emanating from one clamp arm that engage into slots form in the other clamp arm to minimize twisting of the clamp arms relative to one another during squeezing of the clamp closed.

The foregoing has outlined some of the pertinent objects of the invention. These objects should be construed to be merely illustrative of some of the more prominent features and applications of the intended invention. Many other beneficial results can be attained by applying the disclosed invention in a different manner or modifying the invention within the scope of the disclosure. Accordingly, other objects and a fuller understanding of the invention may be had by referring to the summary of the invention and the detailed description of the preferred embodiment in addition to the scope of the invention defined by the claims taken in conjunction with the accompanying drawings.

SUMMARY OF THE INVENTION

For the purpose of summarizing the invention, this invention comprises a clamp for flexible tubing such as medical tubing or micro-tubing. The clamp comprises a clam-shell design having lateral non-opposing sidewalls that prevent the micro-tubing from bending out from under the mating clamping anvils when closed. Unlike the lateral opposing sidewalls of prior art clamps such as is shown in FIG. 1, the lateral non-opposing sidewalls of the clamp of the present invention are non-opposing lateral sidewalls that may be injection molded without the use of additional slides that are otherwise needed to injection mold the prior art opposing sidewalls shown in FIG. 1.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be had to the following detailed description taken in connection with the accompanying drawings in which.

Similar reference characters refer to similar parts throughout the several views of the drawings.

DETAILED DESCRIPTION OF THE PREFERRED EMBODIMENT

Referring to FIGS. 2-5, the tubing clamp 10 of the invention comprises an upper arm 12 and a lower arm 14 flexibly hinged together by a living hinge 16 to define a clam-shell design.

The upper arm 12 comprises a generally flat top configuration 18 with a terminal portion 20. Extending downwardly underneath the flat upper configuration 18 is a generally triangular-in-cross-section upper portion 22 defining a transverse upper anvil 24, preferably with a cross-sectional rounded edge in the form of a circular segment CS. Similarly, the lower arm 14 comprises a generally flat bottom configuration 26 with a terminal portion 28 extending upwardly for removable engagement with the terminal portion 20 of the upper arm 12. Extending upwardly from the flat lower configuration 26 is a generally triangular-in-cross-section lower portion 30 defining a transverse lower anvil 32, preferably with a cross-sectional rounded edge in the form of a circular segment CS.

The living hinge 16 comprises an aperture 34 and the terminal portion 28 of the lower arm 14 comprises another aperture 36 in alignment with one another allowing the tubing (shown in phantom as reference numeral 38) to be clamped threaded therethrough and positioned between the anvils 24 and 32.

The anvils 24 and 32 move generally parallel to one another when the upper arm 12 and lower arm 14 are squeezed together against the inherent resilient memory of the living hinge 16 whereupon the tubing 38 is squeezed between the anvils 24 and 32 to obstruct, or completely close-off, fluid flow through the tubing 38. It is noted that the circular segments CS of the anvils 24 and 32 are preferably aligned parallel with one another such that the tubing 38 is squeezed precisely closed between the anvils 24 and 32.

Without departing from the spirit and scope of the invention, the terminal portions 20 and 28 may comprise a variety of configurations to completely or partially obstruct fluid flow through the tubing 38. As shown, for complete obstruction, the lower terminal portion 28 may comprise a single toothed rack 40 formed on the inward portion of the lower terminal portion 28 of the lower arm 14. The upper terminal portion 22 comprises a pawl 42. The leading edge of the pawl 42 is aligned for engagement with the tooth of the rack 40. When the upper and lower arms 12 and 14 are grasped by a person's hand and squeezed together such that the anvils 24 and 32 tightly squeeze the tubing 38 to close-off fluid flow, the leading edge of the pawl 42 removeably snaps under the tooth of the rack 40 to secure the anvils 24 and 32 is their closed position.

Alternatively, for partial to complete obstruction of fluid flow, the inward portion of the lower terminal portion 28 may comprise a plurality of teeth (not shown) along the rack 40 for sequential engagement by the leading edge of the pawl 42 such that the anvils 24 and 32 gradually squeeze the tubing 38 to initially partially then completely obstruct fluid flow as the anvils 24 and 32 are ratcheted toward one another upon sequential engagement of the leading edge of the pawl 42 along the teeth of the rack 40.

It is noted that the upper configuration 18 may comprise a series of parallel transverse ridges 44 on the upper surface thereof to facilitate better gripping by the person's thumb during such squeezing of the arms 12 and 14 together.

To open the clamp 10, the terminal portion 28 is pushed forwardly by a person's thumb to disengage the leading edge of the pawl 42 from the tooth of the rack 40 whereupon the inherent resilient memory of the living hinge 16 causes the upper and lower arms 12 and 14 (and their respective anvils 24 and 32) to move apart and no longer squeeze the tubing 38.

The clamp 10 of the present invention may be used with different-sized tubings 38 so long as the diameter of the tubing 38 is smaller than the diameter of the apertures 34 and 36 and is therefore capable of being threaded therethrough. Moreover, micro-tubings 38 (i.e., tubing of a very small diameter) may likewise be used. However, it is known that micro-tubing 38 has the tendency to easily flex and bend and may inadvertently easily bend outside of clamp 10 and away from in between the anvils 24 and 32.

In order to better constrain the micro-tubing 38 between the anvils 24 and 32, the clamp 10 of the invention comprise at least one first sidewall 46 on one side (e.g., right) of the clamp 10 and at least one second sidewall 48 on the other side (e.g., left) of the clamp 10. FIGS. 2A, 3A, 4A and 5A illustrate one embodiment of the clamp 10 wherein only one first sidewall 46 and only one second sidewall 48 are employed whereas FIGS. 2B, 3B, 4B and 5B illustrate another embodiment of the clamp 10 wherein only one first sidewall 46 but two second sidewalls 48 are employed.

The sidewalls 46 and 48 in one embodiment emanate from the lower triangular portion 30. Alternatively, in another embodiment (not shown) the sidewalls 46 and 48 may emanate from the upper triangular portion 22. Still alternatively, in other embodiments (not shown), the first sidewall(s) 46 (e.g., the right sidewall) may emanate from the lower triangular portion 30 and the second sidewall(s) 48 (e.g., the left sidewall) may emanate from the upper triangular portion 22, or vice versa.

The sidewalls 46 and 48 in one embodiment each comprise a generally flat rectangular configuration to define a tubing path between the apertures 34 and 36 such that when clamping micro-tubing 38, the micro-tubing 38 is constrained to be in proper transverse alignment between the anvils 24 and 32 and is prevented from inadvertently bending out from between the anvils 24 and 32 where they would not be properly squeezed closed between the anvils 24 and 32.

In the first embodiment as shown in FIGS. 2A, 3A, 4A and 5A, the single first sidewall 46 emanates upwardly from the side end of the anvil 32 of the triangular portion 30 whereas the single second sidewall 48 emanates upwardly from the side end of the forward sloped surface 30FS of the triangular portion 30. Alternatively, in the third embodiment shown in FIG. 6, the single first sidewall 46 emanates upwardly from the anvil 32 of the triangular portion 30 and the single second sidewall 48 emanates upwardly from the rearward sloped surface 30RS of the triangular portion 30.

Figure 4A:
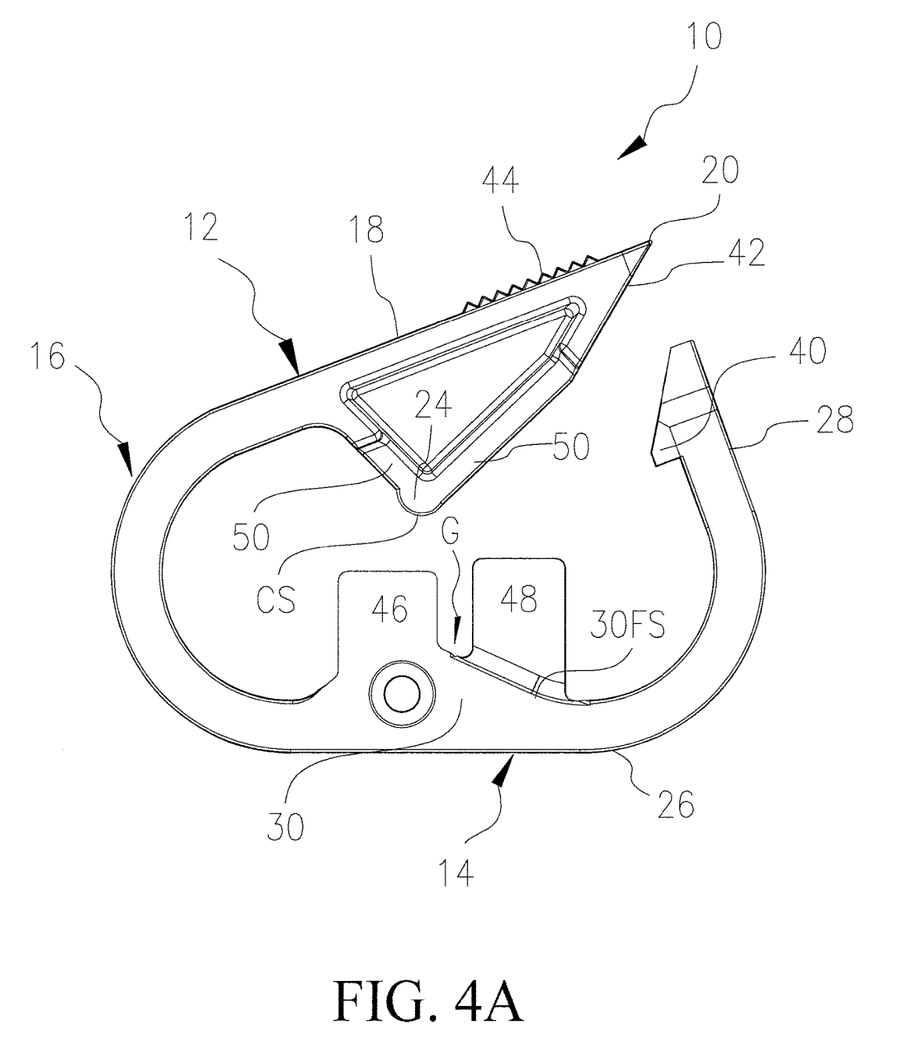
FIG. 4A is a right side view of a first embodiment of the tubing clamp of the invention having two lateral sidewalls that are not directly opposing one another.
Figure 4B:
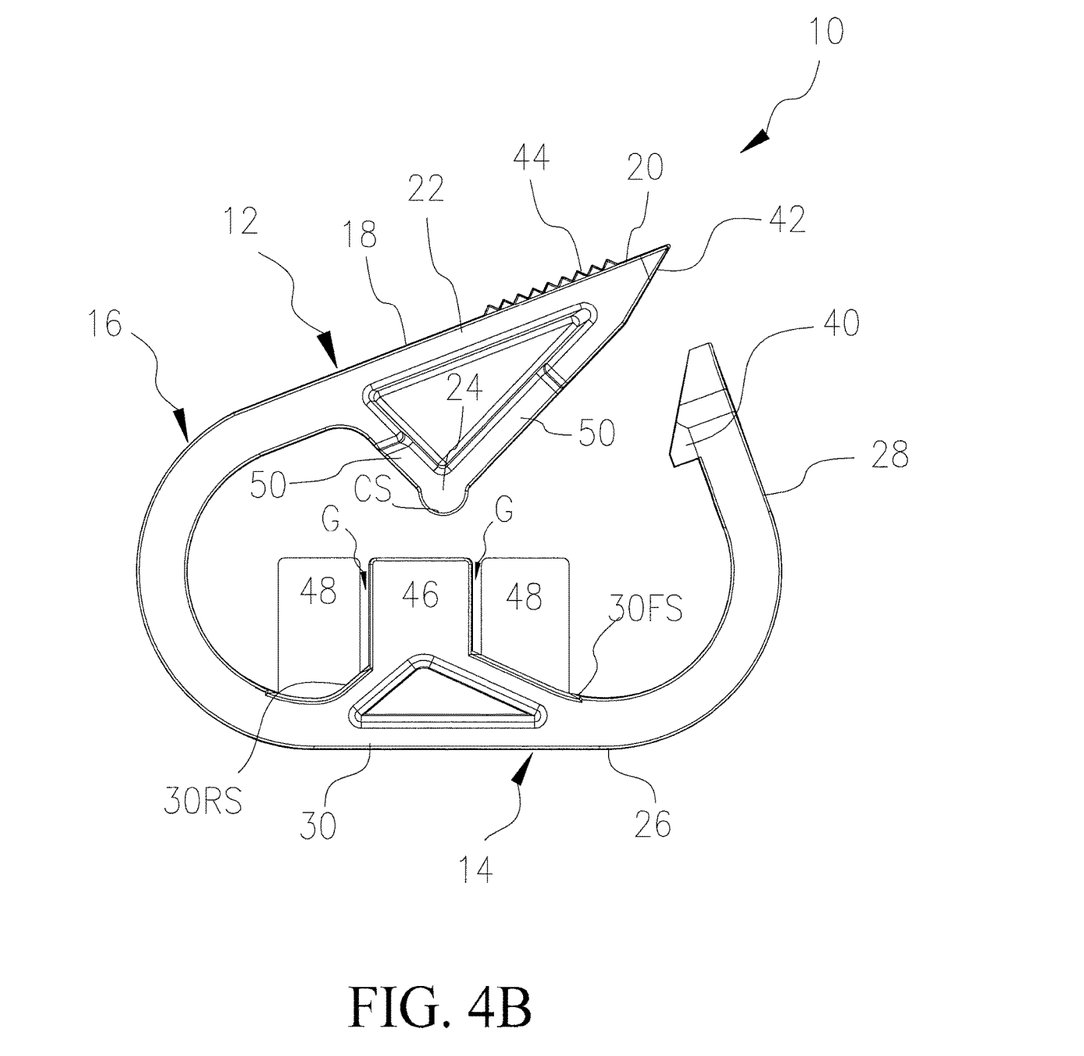
FIG. 4B is a right side view of a second embodiment the tubing clamp of the invention having three lateral sidewalls that are not directly opposing one another.
Figure 5A:
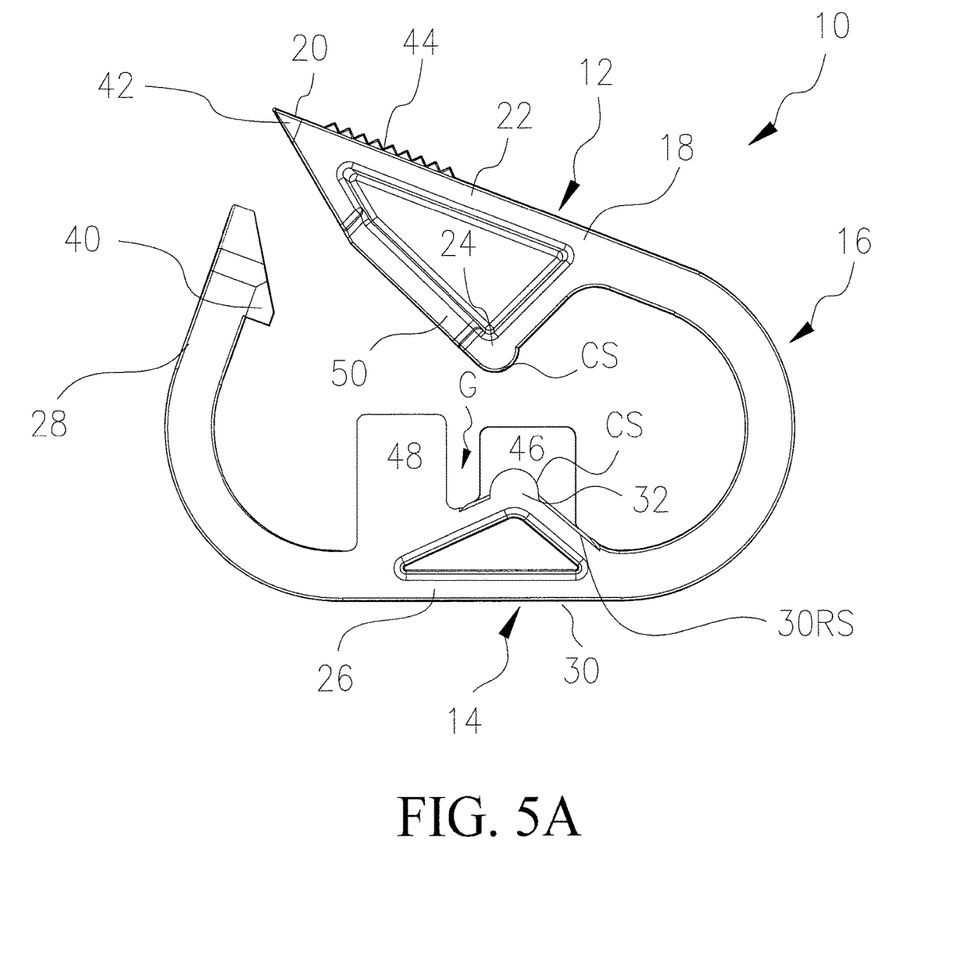
FIG. 5A is a left side view of a first embodiment of the tubing clamp of the invention having two lateral sidewalls that are not directly opposing one another.
Figure 5B:
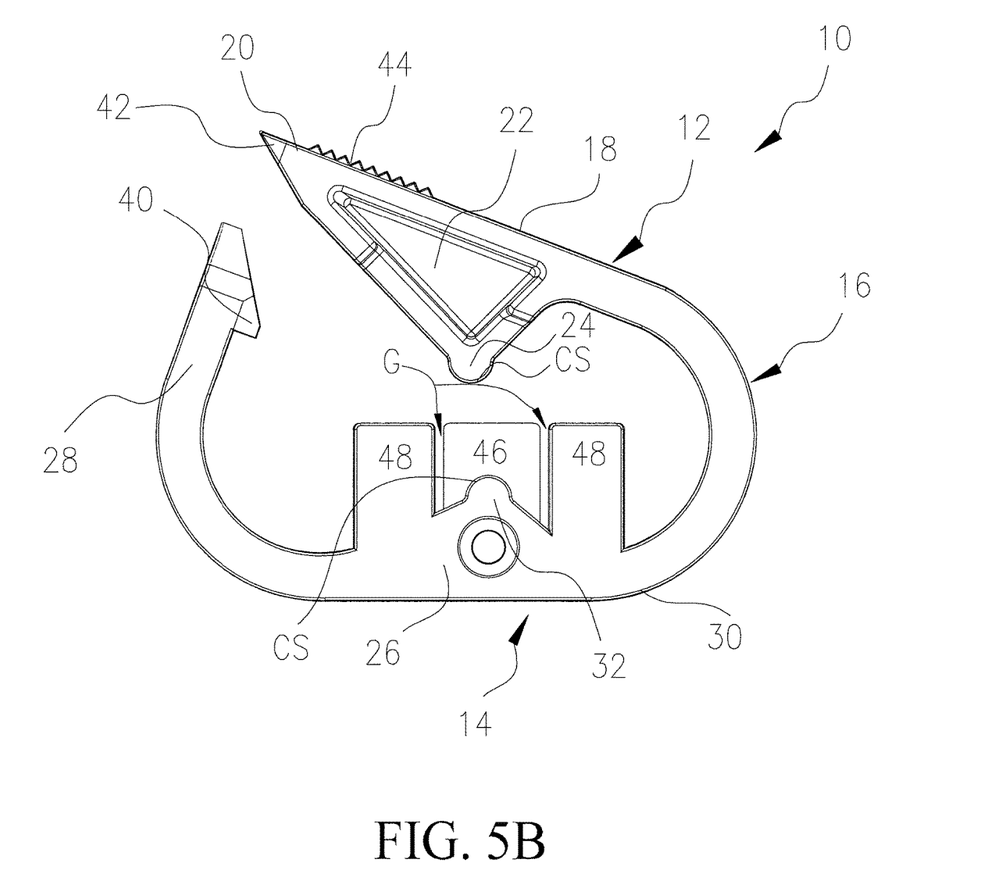
FIG. 5B is a left side view of a second embodiment the tubing clamp of the invention having three lateral sidewalls that are not directly opposing one another.
Figure 6:
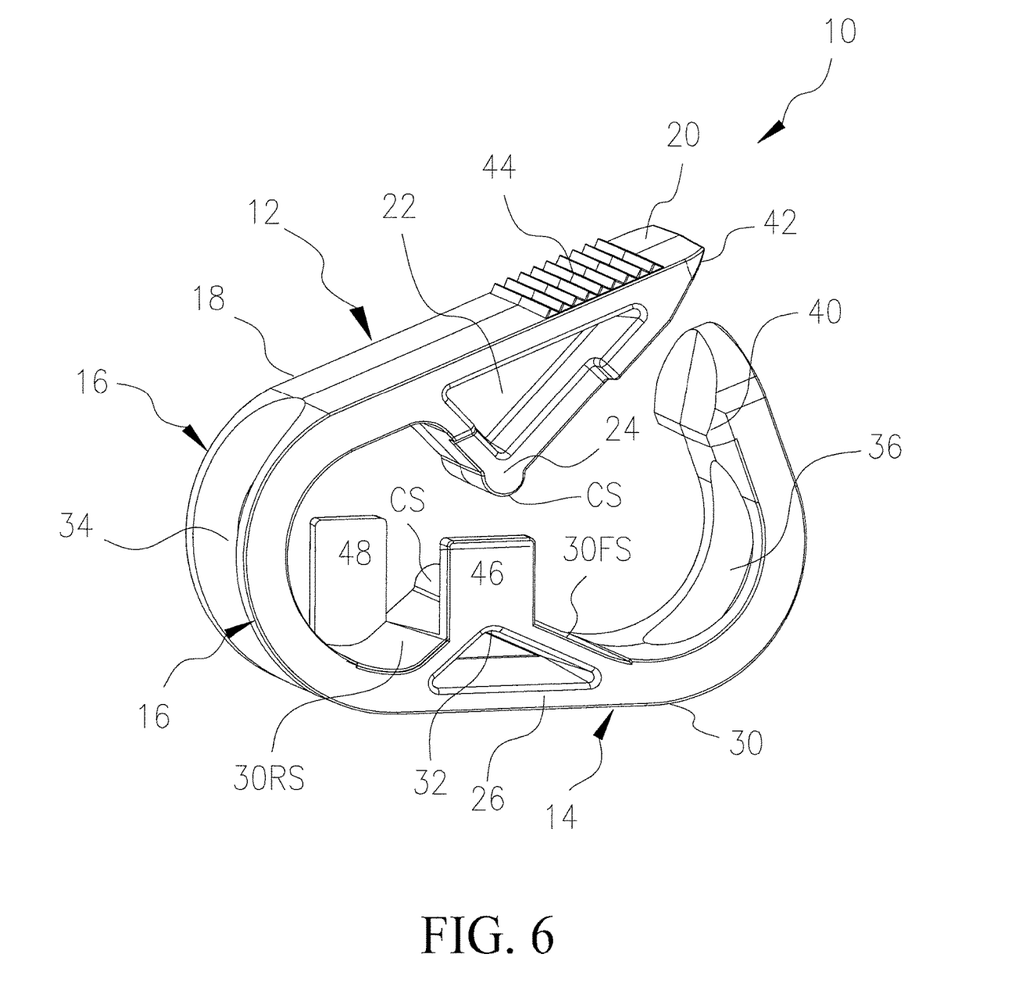
FIG. 6 is a right perspective view of a third embodiment of the tubing clamp of the invention having two lateral sidewalls that are not directly opposing one another.

Unlike the prior art clamps employing opposing sidewalls (see for example FIG. 1), the first and second sidewall(s) 46 and 48 of the clamp 10 of the present invention are not directly aligned opposite one another (i.e., the left first sidewall(s) 46 is not aligned directly across from the right second sidewall(s)). Rather, as best shown in FIGS. 4 and 5, the first and second sidewalls 46 and 48 are non-opposing from one another such that no portion of the first sidewall(s) 46 is directly opposite to any portion of the second sidewall(s) 48 to form a gap G when the clamp 10 is viewed from the side. Importantly, the gap G formed between the non-opposed first and second sidewalls 46 and 48 facilitate injection molding of the clamp 10 by the two halves of a conventional injection mold without the use of slides that would otherwise be necessary were the sidewalls opposing one another as taught by the prior art (see FIG. 1).

The upper arm 12 may comprise first and second side slots 50 and 52 into which the respective first and second sidewalls 46 and 48 may move into as the clamp 10 is squeezed closed by moving the arms 12 and 14 together. Advantageously, the slots 50 and 52 function to better align the upper triangular portion 22 relative to the lower triangular portion 30 upon movement of the arms 12 and 14 together such that the arms 12 and 14 do not otherwise twist during closing and otherwise misalign the anvils 24 and 32 as they are clamped together. A more complete closure of the micro-tubing 38 may therefore be achieved since the anvils 24 and 32 will be more accurately aligned parallel during clamping to more completely obstruct fluid flow through the micro-tubing.

In another embodiment of the invention (not shown), the first and second sidewalls 46 and 48 may emanate from the upper triangular portion 22 whereupon the lower triangular portion 30 may comprise first and second side slots into which the respective first and second sidewalls 46 and 48 may move into as the clamp 10 is squeezed closed.

The present invention includes that contained in the appended claims as well as that of the foregoing description. Although this description has been described in its preferred form with a certain degree of particularity, it should be understood that the present disclosure of the preferred form has been made only by way of example and that numerous changes in the details of construction, combination, or arrangement of parts thereof may be resorted to without departing from the spirit and scope of the invention.

What is claimed is:

1. A tubing clamp, comprising in combination:
   an upper arm and a lower arm flexibly hinged together, said arms including an upper anvil and a lower anvil, respectively;
   at least one first sidewall on one side of the clamp and at least one second sidewall on the other side of the clamp, said first sidewall being spaced apart from said second sidewall defining a longitudinal tubing path therebetween, said sidewalls being non-opposing from one another such that no portion of the first sidewall is directly opposite to any portion of the second sidewall to facilitate injection molding of the clamp;
   said upper anvil and said lower anvil extending transversely relative to said longitudinal tubing path dividing said longitudinal tubing path into a distal portion and a proximal portion; and
   at least a portion of said first sidewall located along said distal portion of said longitudinal tubing path and at least a portion of said second sidewall located along said proximal portion of said longitudinal tubing path.

2. The clamp as set forth in claim 1, wherein a gap is formed between said sidewalls.

3. The clamp as set forth in claim 2, wherein said first and second sidewalls emanate from one of said arms.

4. The clamp as set forth in claim 3, wherein the other one of said arms includes first and second side slots into which respective first and second sidewalls move into as the clamp is squeezed closed.

5. The clamp as set forth in claim 3, wherein said first sidewall emanates from said anvil of respective said arm.

6. The clamp as set forth in claim 5, wherein said arm from which said first sidewall emanates, further comprises a triangular portion defined by said anvil, a forward sloped surface and a rearward sloped surface.

7. The clamp as set forth in claim 6, wherein said second sidewall emanates from said forward sloped surface.

8. The clamp as set forth in claim 6, wherein said second sidewall emanates from said rearward sloped surface.

9. The clamp as set forth in claim 1, wherein said upper arm and said lower arm are flexibly hinged together by a living hinge.

10. The clamp as set forth in claim 9, further including an aperture formed in said living hinge.

11. The clamp as set forth in claim 1, wherein said at least one first sidewall on one side of the clamp comprises a single first sidewall and wherein said at least one second sidewall on the other side of the clamp comprises two second sidewalls.

12. The clamp as set forth in claim 1, wherein said sidewalls comprise a flat rectangular configuration.

13. The clamp as set forth in claim 1, wherein said anvils each comprises a circular segment whose respective axes are in parallel alignment with one another.

14. The clamp as set forth in claim 1, wherein said arms each comprise terminal portions to engage one other to completely or partially obstruct fluid flow through tubing positioned longitudinally within said longitudinal tubing path and transversely between said anvils when said arms are moved toward one another.

15. The clamp as set forth in claim 14, wherein one of said terminal portions comprises a toothed rack that removably engages a pawl of the other said terminal portion.

16. The clamp as set forth in claim 15, wherein said toothed rack comprise a single tooth.

* * * * *